United States Patent [19]

Verri

[11] Patent Number: 5,626,825

[45] Date of Patent: May 6, 1997

[54] PROCESS FOR THE PURIFICATION OF MAGNESIUM HYDROXIDE

[75] Inventor: Giancarlo Verri, Segrate, Italy

[73] Assignee: V.B.C. S.r.l., Milan, Italy

[21] Appl. No.: 497,898

[22] Filed: Jul. 3, 1995

[30] Foreign Application Priority Data

Jul. 21, 1994 [IT] Italy .................. MI94A1543

[51] Int. Cl.$^6$ ........................................ C01F 5/14
[52] U.S. Cl. ................................ 423/155; 423/636
[58] Field of Search ........................... 423/155, 636

[56] References Cited

U.S. PATENT DOCUMENTS

| | | | |
|---|---|---|---|
| 3,800,032 | 3/1974 | Eberle et al. | 423/636 |
| 4,693,872 | 9/1987 | Nakaya et al. | 423/636 |
| 5,461,101 | 10/1995 | Rothon et al. | 423/636 |

FOREIGN PATENT DOCUMENTS

| | | | |
|---|---|---|---|
| 120514 | 7/1983 | Japan | 423/636 |

*Primary Examiner*—Wayne Langel
*Attorney, Agent, or Firm*—Oblon, Spivak, McClelland, Maier & Neustadt, P.C.

[57] ABSTRACT

A process for preparing magnesium hydroxide having high purity which comprises dispersing the raw product in water, under stirring, then adjusting the pH to a value comprised between 10.0 and 14.0; adding a chelating agent and separing the resulting phases.

9 Claims, No Drawings

PROCESS FOR THE PURIFICATION OF MAGNESIUM HYDROXIDE

The present invention relates to a process for the purification of magnesium hydroxide.

Magnesium hydroxide is mainly obtained by cave extraction, by sea brine extraction, by reaction with NaOH or $Ca(OH)_2$, or by sea water extraction, making the magnesium hydroxide therein contained precipitate with a strong base and then extracting by known techniques (see the booklet of Sardamag Spa, January 1994—"Production of sea water magnesite for refractory purposes", Moscuzza et al.; Villavecchia Eigenmann: vol. 4, pag. 2006).

The natural magnesium hydroxide extracted from caves shows a relatively high purity of 96–98%; at present the low extracting cost, the great availability and the high purity make this product preferable in respect with the product extracted by sea water, for some peculiar applications or as starting material for further purification; however the qualitative and crystalline unevennesses make this source limiting as to pharmaceutics and as flame retarder, in the industry of plastics and cables and also in the industry of cosmetics and detersives.

The magnesium hydroxide extracted from sea brine, which is a concentrated solution containing magnesium salts such as, for instance, chlorides, is obtaining by reaction with a strong base, for instance NaOH or $Ca(OH)_2$.

The magnesium hydroxide synthesised from sea water is obtained by precipitation with a base, for instance calcium or sodium hydroxide, effecting consecutive washings with inorganic acids of low price, such as for instance HCl, $H_2SO_4$, and then solubilizing again the hydroxide and recrystallizing it with the help of great quantities of washing water, thereby obtaining improvements of the titer.

Because of some cationic and anionic polluting substances, due to acid and basic reagents used and to other impurities, for instance borates, a product having a purity lower than that one obtained for the product extracted from the caves is obtained.

The use of inorganic acids and bases gives a further advantage because of the difficulty of the disposal of the effluents, in view of their great harmfulness for the environment.

Big volumes of water and acids, which make rather high the cost of such a process, are furthermore used.

The anions normally contained in sea water, which are not eliminated during the purification process, obviously reduce the titer of the final product.

Further, magnesium hydroxide easily reacts with the carbon dioxide present either in the water or in the air forming magnesium carbonate (and eventually calcium carbonate if calcium hydroxide is used for the precipitation) and thereby further lowering the purity thereof: the titer of magnesium obtained is in fact hardly higher than 93/95% (expressed as MgO).

The product obtained is therefore utilizable only in hose applications where a high purity is not required, for instance the hydroxide thereby obtained, under the form of the oxide, can be used as a refractory.

A thermic process, where the hydroxide is calcined and transformed into the oxide and then rehydrated to be retransformed into the hydroxide, is used to further purify magnesium hydroxide from sea water.

With such a process, high purities, to 99% too, are obtained; however, the investment and energy costs are so high that make the carrying out of such a process on an industrial scale disadvantageous.

Another process for the purification of magnesium hydroxide which carries to obtaining a product showing a purity comparable with that one resulting from the thermic process, is carried out by ion exchange, selective, resins such as MITSUBISHI DIAION CRB 02 and ROHM AND HAAS IR 120 and IRA 400, after resolubilising the hydroxide by acidifying.

However, the high cost of the resins and of the reagents for their continuous regeneration, together with the complexity of the plants and of their management besides to the big volumes of water and acids and bases used, make such process disadvantageous from an industrial point of view even if it is convenient only for the production of extremely little quantities also because of the high cost thereof.

A purpose of the present invention is to realise an easily feasible process, which do not involve disposal problems or which do not represent, even potentially in time, a damage for the environment anyway, which is cheap and convenient from the industrial point of view.

Another purpose of the present invention is to disclose a process for the purification of magnesium hydroxide by which a purity even higher than 98% is obtained, which shows crystalline uniformity and qualitative constancy.

These and other purposes, which will be evident to the skilled in the art by reading the specification and the following embodiments, are obtained carrying out a process for preparing magnesium hydroxide substantially pure, from raw magnesium hydroxide, which comprises dispersing the raw product into water, under stirring, then adjusting pH to a value between 10,0 and 14,0; adding a chelating agent and separing the resulting phases, optionally further washing with water the product thereby obtained.

The starting product can be magnesium hydroxide extracted from sea brine or from sea water just prepared or even packed and being some months old.

Preferably, the ratio between the raw product and water is comprised between 1:2 and 1:30 by weight, particularly between 1:5 and 1:10 by weight.

Said dispersion is carried out at a temperature comprised between 5° C. and 95° C., preferably between 20° C. and 60° C.

Preferably the ratio between the pure magnesium hydroxide and the pure chelating agent is comprised between 0,01 and 0,5 by weight.

After separing the phases an organic acid selected from the group consisting of citric, tartaric, acetic acid and the like is preferably added.

Chelating agents suitable for the purposes of the present invention are selected from the group consisting of ethylene diamine tetraacetic acid (EDTA) and the salts thereof with alkaline metals.

Also preferably, after said dispersion, in the process of the present invention, the pH is raised adding a base selected from the group consisting of the alkaline metals hydroxides and ammonia and organic bases such as amines as for instance triethanolamine.

The magnesium hydroxide obtained by the process of the present invention shows a purity of at least 98%; such value may be obviously raised carrying out more washings: a magnesium hydroxide having a purity equal or higher than 99% is obtained with an average of three washings, as it comes out from the following examples.

The product obtained carrying out the process of the present invention, thanks to the high purity and to crystalline uniformity and qualitative constancy, is particularly suitable to be used in pharmaceutics, for instance as an antiacid, mild laxative, etc. and in the industry of plastics and of cables, as flame retarder and also in the industry of cosmetics and of detersives, even if it can be used, obviously, for all the known applications: for instance, as a refractory, as a cement additive, for the treatment of water, as clarifying agent of water, as an intermediate for the industrial production of magnesium, etc.

The process of the invention is easily feasible and, given its operative simpleness, involves a reduced use of manpower.

Further, the present process permits a remarkable economic saving, being therefore particularly suitable for the realisation on an industrial scale.

It is also suitable for the production of magnesium oxide obtained by burning and calcining the magnesium hydroxide resulting therefrom.

The process of the invention does not show any problem of the disposal of the effluents which, given their nature, may be discharged directly into the sea or in the sewers without the need of preliminary treatments.

The following embodiments of the process of the present invention are merely meant to illustrate and not to limit it in any way.

All the percentages are expressed by weight unless otherwise specified.

The specific surface is the surface area per weight or volume unit.

EXAMPLE 1

8.400 Kg of the starting material, being some months old and already packed, which is under the form of compact blocks with an average solid content of 75&, the analysis of some of the impurities thereof being the following:

| % CaO | % $SO_3$ | % $B_2O_3$ | % $Cl^-$ | % $CO_2$ |
|---|---|---|---|---|
| 2.00 | 0.80 | 0.25 | 1.20 | 2.00 |

(on the hydroxide base, titer of 93.54%), are introduced in a kneader with 8400 Kg of demineralised $H_2O$. In the meantime, 19,200 Kg of demineralised $H_2O$ are introduced in a reactor heated to 60°±5° C.; the initial dispersion is introduced in the reactor and 360 l of 30% NaOH are added to a pH of about 13.29. 360 l of the sodium salt of a 40% solution of ethylene diamine tetraacetic acid (EDTA) are added, always under stirring, and letting reacting for 8 hours at the temperature of 60°±5° C.

The specific surface initially measured was 12.0 $m^2/g$. Centrifuging, using a horizontal continuous centrifuge of the ALFA-LAVAL/SHARPLES SUPER-D-CANTER type, and separing the two phases obtained are carried out. The slurry thereby obtained shows an average solid content of 68%.

The analysis of the product thereby obtained gave the following results:

| % CaO | % $SO_3$ | % $B_2O_3$ | % $Cl^-$ | % $CO_2$ |
|---|---|---|---|---|
| 1.20 | 0.40 | 0.15 | 0.20 | 1.10 |

(on the hydroxide base, specific surface 14.0 $m^2/g$, titer= 96.74%). As it comes out from the results, a reduction of 40% of CaO, 50% of sulphates, 40% of borates, 83% of chlorides and 45% of carbonates was obtained.

The process is repeated yet working at room temperature, about 20° C., introducing in the reactor 8760 Kg of 68% magnesium hydroxide previously obtained with 27240 Kg of demineralised water and, at pH 12.68, 220 Kg of 40% NaEDTA are added. Working as before, letting reacting for 8 hours, is carried out.

Centrifuging and separing the phases are carried out.

The analysis of some of the impurities of the solid phase thereby obtained gave the following results:

| % CaO | % $SO_3$ | % $B_2O_3$ | % $Cl^-$ | % $CO_2$ |
|---|---|---|---|---|
| 0.80 | 0.30 | 0.10 | 0.06 | 0.30 |

(on the hydroxide base, the total titer is 98.23%).

As it comes out from the results, the total reduction is 60% of CaO, 62.5% of sulphates, 60% of borates, 95% of chlorides and 85% of carbonates.

EXAMPLE 2

The process according the Example 1 is repeated, yet working at room temperature after having brought the initial dispersion to a volume of 36,000 l. 12,192 Kg of citric acid in powder are added and, at pH 10.84, 220 l of 40% NaEDTA are added.

The analysis of the product thereby obtained gave the following results:

| % CaO | % $SO_3$ | % $B_2O_3$ | % $Cl^-$ | % $CO_2$ |
|---|---|---|---|---|
| 0.06 | 0.22 | 0.09 | 0.04 | 0.02 |

(on the hydroxide base, titer 98.72%).

EXAMPLE 3

7,200 Kg of magnesium hydroxide, having an average solid content of 60%, the analysis of some of the impurities thereof being the following:

| % CaO | % $SO_3$ | % $B_2O_3$ | % $Cl^-$ | % $CO_2$ |
|---|---|---|---|---|
| 0.50 | 0.90 | 0.30 | 1.14 | 0.30 |

(titer on the hydroxide base 96.65%), are introduced in a kneader with 7,200 Kg of demineralised water at room temperature and introduced in the reactor bringing the volume to 36,000 l under stirring; 360 l of 40% NaEDTA are added at a pH of 10.11 and allowed to react for 5 hours.

Centrifuging and separing the phases are carried out. The slurry obtained is redispersed in the reactor up to 36,000 l and 60 Kg of NaOH up to a pH of 12.43 are added. Allowing to reacting for 8 hours and separing again by centrifuging is carried out.

The slurry obtained from the separation of the solid phase is dispersed again up to 30,000 l and 86.4 Kg of 30% NaOH, up to a pH of 12.83, are added.

Heating to 60°±5° C. and allowing to react for 5 hours under stirring is carried out.

The phases are separated following the way described in the Example 1 and a product, the analysis thereof gave the following results, is obtained:

| % CaO | % $SO_3$ | % $B_2O_3$ | % $Cl^-$ | % $CO_2$ |
|---|---|---|---|---|
| 0.19 | 0.20 | 0.19 | 0.02 | 0.07 |

(on the hydroxide base, titer: 99.12%).

I claim:

1. A process for preparing substantially pure magnesium hydroxide from raw magnesium hydroxide, which comprises dispersing raw magnesium hydroxide in water, under stirring to form a dispersion; bringing the pH of the dispersion to a value between 10.0 and 14.0; adding a chelating agent to the dispersion; and separating the resulting phases to isolate a substantially pure magnesium hydroxide product; and optionally washing said product with water.

2. A process according to claim 1, wherein the ratio between the raw magnesium hydroxide and water is between 1:2 and 1:30 by weight.

3. A process according to claim 1, wherein said dispersion is carried out at a temperature between 5° C. and 95° C.

4. A process according to claim 1, wherein said dispersion is carried out at a temperature between 20° C. and 60° C.

5. A process according to claim 1, wherein the ratio of pure magnesium hydroxide to pure chelating agent is between 0.01 and 0.5 by weight.

6. A process according claim 1, wherein after said dispersion is formed, the pH is raised by adding an inorganic or organic base, selected from the group consisting of alkali metal hydroxides and organic amines.

7. A process according to claim 1, wherein said chelating agent is selected from the group consisting of ethylene diamine tetraacetic acid and the salts thereof with alkaline metals.

8. A process according to claim 1, wherein after separating the phases the pH is lowered by adding an organic acid selected from the group consisting of citric, tartaric and acetic acid.

9. A process according to claim 1, wherein the ratio between the raw magnesium hydroxide and water is between 1:5 and 1:10 by weight.

* * * * *